(12) United States Patent
Strölin

(10) Patent No.: US 11,293,631 B2
(45) Date of Patent: Apr. 5, 2022

(54) SURGICAL LIGHT HAVING MEANS FOR MEASURING DISTANCE

(71) Applicant: Karl Leibinger Medizintechnik GmbH & Co. KG, Mühlheim (DE)

(72) Inventor: Joachim Strölin, Mühlheim (DE)

(73) Assignee: Karl Leibinger Medizintechnik GmbH & Co. KG, Mühlheim (DE)

( * ) Notice: Subject to any disclaimer, the term of this patent is extended or adjusted under 35 U.S.C. 154(b) by 420 days.

(21) Appl. No.: 16/332,260

(22) PCT Filed: Aug. 29, 2017

(86) PCT No.: PCT/EP2017/071593
§ 371 (c)(1),
(2) Date: Mar. 11, 2019

(87) PCT Pub. No.: WO2018/046339
PCT Pub. Date: Mar. 15, 2018

(65) Prior Publication Data
US 2019/0203920 A1 Jul. 4, 2019

(30) Foreign Application Priority Data

Sep. 12, 2016 (DE) .......................... 102016117067.4

(51) Int. Cl.
*F21V 23/04* (2006.01)
*A61B 90/35* (2016.01)
(Continued)

(52) U.S. Cl.
CPC .......... *F21V 23/0492* (2013.01); *A61B 90/30* (2016.02); *A61B 90/35* (2016.02);
(Continued)

(58) Field of Classification Search
CPC ... A61B 90/30; A61B 2090/309; A61B 90/35; A61B 2034/2051; A61B 2050/005;
(Continued)

(56) References Cited

U.S. PATENT DOCUMENTS 4,884,008 A 11/1989 Bossier et al.
5,038,261 A * 8/1991 Kloos ..................... F21S 8/043
362/286

(Continued)

FOREIGN PATENT DOCUMENTS

| CN | 1662771 A | 8/2005 |
|---|---|---|
| CN | 101238326 A | 8/2008 |

(Continued)

OTHER PUBLICATIONS

May 3, 2017—DE 102016117067.4—German Search Report.
(Continued)

*Primary Examiner* — William J Carter
(74) *Attorney, Agent, or Firm* — Banner & Witcott, Ltd.

(57) ABSTRACT

The invention relates to a surgical light comprising a light unit which has a plurality of light sources individually accommodated in a housing, wherein each light source is arranged and oriented in such a way that the light source produces a light beam in an energized state; an anchoring element which is prepared for fastening to a ceiling, a wall or a floor of a room; and a retaining arm system which connects the light unit slidably and/or pivotably to the anchoring element, wherein a position detection device is arranged and designed in such a way that, in the operating state, the position detection device determines a distance of a reference section of the light unit or of the retaining arm system from the ceiling.

15 Claims, 1 Drawing Sheet

(51) Int. Cl.
*F21V 21/28* (2006.01)
*F21V 21/40* (2006.01)
*A61B 90/30* (2016.01)
*H05B 45/20* (2020.01)
*F21V 21/29* (2006.01)
*F21W 131/205* (2006.01)
*F21W 131/202* (2006.01)
*F21Y 115/10* (2016.01)

(52) U.S. Cl.
CPC .............. *F21V 21/28* (2013.01); *F21V 21/29* (2013.01); *F21V 21/403* (2013.01); *F21V 23/0442* (2013.01); *H05B 45/20* (2020.01); *A61B 2090/309* (2016.02); *F21W 2131/202* (2013.01); *F21W 2131/205* (2013.01); *F21Y 2115/10* (2016.08)

(58) Field of Classification Search
CPC ........ A61B 2050/314; A61B 2090/061; A61B 2090/067; A61B 50/13; A61B 50/36; A61B 50/362; F21W 2131/205; F21W 2131/202; Y10S 128/00; Y10S 600/00; Y10S 601/00; Y10S 604/00; Y10S 606/00; Y10S 607/00
See application file for complete search history.

(56) References Cited

U.S. PATENT DOCUMENTS

| | | |
|---|---|---|
| 6,880,957 B2 | 4/2005 | Walters |
| 8,888,696 B2 * | 11/2014 | Marka .................... A61B 90/30 362/220 |
| 2003/0161152 A1 | 8/2003 | Jesurun et al. |
| 2009/0122536 A1 | 5/2009 | Scholz |
| 2011/0015492 A1 | 1/2011 | Mangiardi et al. |
| 2012/0161647 A1 * | 6/2012 | Fornasiero ............. A61B 90/35 315/158 |
| 2015/0137686 A1 | 5/2015 | Aliakseyeu et al. |
| 2015/0145419 A1 | 5/2015 | Lashina et al. |

FOREIGN PATENT DOCUMENTS

| | | |
|---|---|---|
| DE | 39 33 596 A1 | 4/1991 |
| DE | 102 25 077 A1 | 12/2003 |
| DE | 203 16 755 U1 | 3/2005 |
| EP | 0 422 331 A2 | 4/1991 |
| EP | 2 902 698 A1 | 8/2015 |
| RU | 2406020 C2 | 12/2010 |
| RU | 2623491 C2 | 6/2017 |

OTHER PUBLICATIONS

Nov. 13, 2017—PCT/EP2017/071593—IRS & WO.
Dec. 11, 2020—(RU) Decision—App 2019109715—Eng Tran.
Apr. 14, 2020—(CN) Office Action—App 201780056043.3—with machine translation.
Apr. 14, 2020—(CN) Search Report—App 201780056043.3—with machine translation.
Dec. 20, 2021 (EP) Communication—Appl No. 17768372.9—English Machine Translation.

* cited by examiner

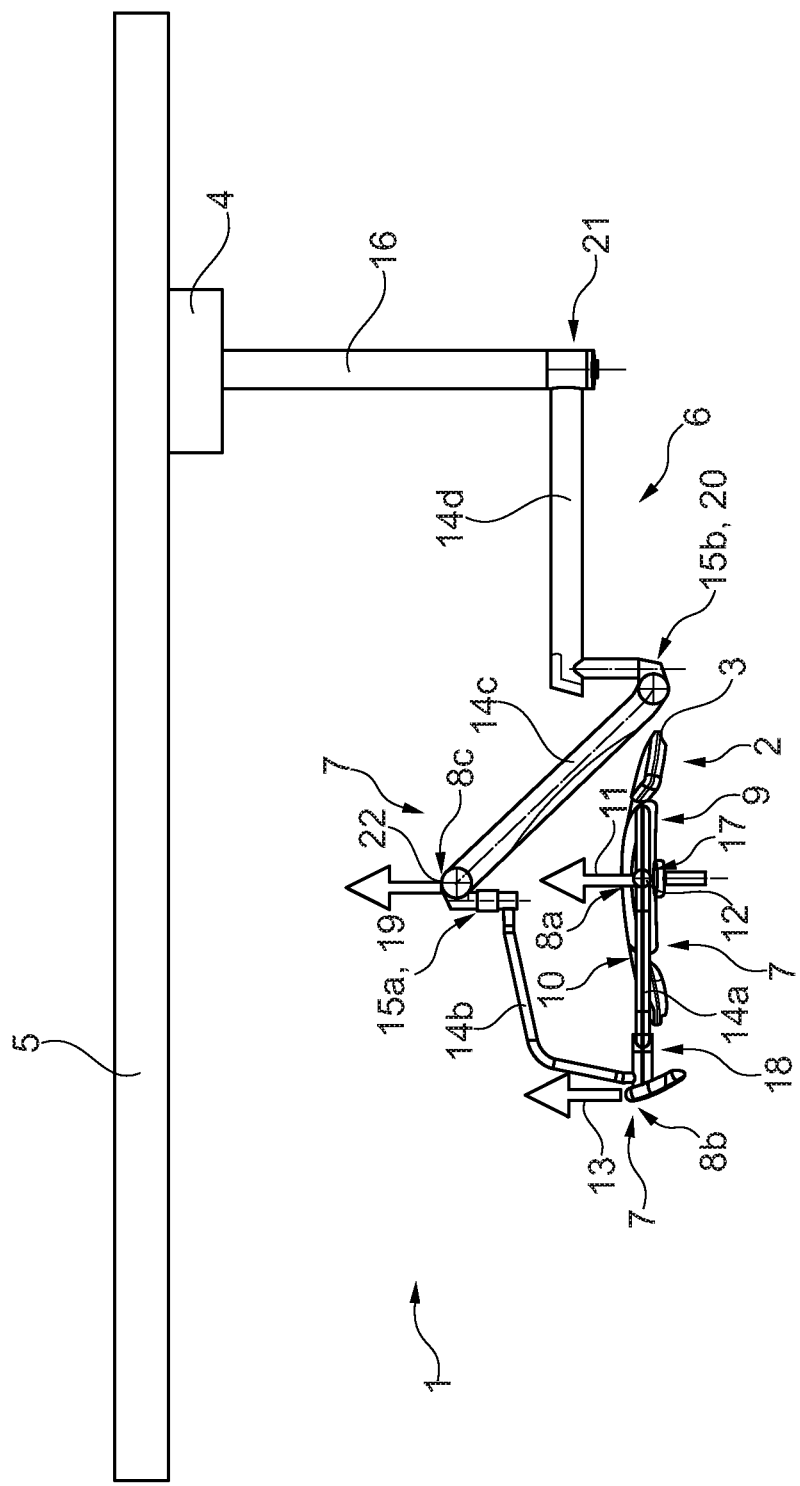

SURGICAL LIGHT HAVING MEANS FOR MEASURING DISTANCE

CROSS-REFERENCE TO RELATED APPLICATIONS

This application is a U.S. National Stage application under 35 U.S.C. § 371 of International Application PCT/EP2017/071593 (published as WO 2018/046339 A1), filed Aug. 29, 2017, which claims the benefit of priority to Application DE 102016117067.4, filed Sep. 12, 2016. Benefit of the filing date of each of these prior applications is hereby claimed. Each of these prior applications is hereby incorporated by reference in its entirety.

The invention relates to a surgical light comprising a light unit which has a plurality of light sources individually accommodated in a housing, wherein each light source is arranged and oriented in such a way that the light source produces a light beam (preferably directed to a joint imaginary horizontal lighting plane) in an energized state, an anchoring element which is prepared for fastening to a ceiling, a wall or a floor of a room, as well as a retaining arm system which connects the light unit slidably and/or pivotably to the anchoring element.

From the state of the art, generic surgical lights are already basically known. For example, U.S. Pat. No. 6,880,957 B2 discloses a lighting device with electronic shadow compensation.

It is a requirement for optimum lighting adjustment of the surgical light that the distance between the light unit of the surgical light and the operating field which is formed e.g. by a support surface of an operating table should be known. If the position of the light unit is varied relative to the operating field during an operation, the lighting adjustment has to be frequently readjusted/tracked as quickly as possible.

Therefore, it has been considered already to attach distance sensors to surgical lights for detecting the direct distance between the respective light unit and the operating field. Said sensors measure the distance between the surgical light and the operating field at intervals and thus enable the lighting setting to be quickly readjusted. Direct measurement of the distance between the surgical light and the operating field/the light field is relatively difficult, however, as frequently disturbing objects such as heads or hands of the operating surgeons, enter into the measuring field detection area of the used distance sensors toward the operating field, while the surgical light is activated. Frequently, this results in faulty measurement as well as in undesired readjustment of the lighting setting of the surgical light.

Thus, it is the object of the present invention to eliminate said drawbacks known from the state of the art and, especially, to provide a surgical light which readjusts its lighting setting as quickly and precisely as possible when the position of the light unit is varied.

According to the invention, this object is achieved by the fact that a position detection device is arranged and designed in such way that, in the operating state, it determines a distance of a reference section of the light unit or of the retaining arm system from the ceiling.

This permits largely failure-free reference measurement for determining a distance relative to a ceiling. This design renders the surgical light less susceptible to objects protruding ahead of the operating field and a largely failure-free operation of the surgical light can be realized.

Further advantageous embodiments are claimed in the subclaims and will be detailed in the following.

When the position detection device is arranged on the light unit or the retaining arm system, it can be integrated particularly skillfully in the surgical light.

When the position detection device includes a distance detection sensor, the structure of the surgical light is especially simple. In that case, the ceiling preferably immediately forms a large area which is detected especially easily by the distance detection sensor. Then the distance detection sensor is disposed, in the mounting position of the surgical light, preferably at a portion (adjustable in position/height) of the retaining arm system or of the light unit which is directed upwardly in space.

It is of particular advantage when the housing (of the light unit) includes a curved or bent extension, with the light sources generating light beams which are emitted toward a joint light emission side of the housing (from the light unit). The light emission side is also referred to as lower side of the light unit. Thus, the position detection device is especially efficient.

In this context, it is moreover advantageous when the position detection device includes a first distance detection sensor which is arranged on a side facing away from the light emission side, i.e. an upper side, of the housing (and further preferred is oriented with its measuring field detection area opposite to the light beams of the light sources/is directed away from the light beams of the light sources). Thus, the structure of the operating light is as simple as possible, with the position detection device being skillfully integrated in the light unit.

When the first distance detection sensor is arranged in the area of a (height-adjustable) pivot axis about which the light unit is pivoted relative to the retaining arm system, the first distance detection sensor is disposed at a position of the light unit which is covered by any objects as seldom as possible toward the ceiling.

When the position detection device includes, in addition or as an alternative to the first distance detection sensor, a second distance detection sensor provided at the retaining arm system, the reliability of determining the position of the light unit is further improved.

In this context, again it is useful when the second distance detection sensor is arranged on a (height-adjustable) universal joint of the retaining arm system. In this area the distance can be measured especially precisely so that the susceptibility of detection is further reduced.

Also, it is advantageous when the position detection device includes, in addition or as an alternative to the first and/or second distance detection sensor, an angle detection sensor (preferably disposed in the retaining arm system) which is preferably designed and arranged so that it detects an angle/an angular position of a support arm portion of the retaining arm system arranged pivotably relative to the anchoring element (relative to a reference line/axis). The distance measurement is further simplified by reference to a corresponding angle of the supporting arm portion which preferably is a height-adjustable spring arm of the retaining arm system.

It is of advantage when the position detection device is connected for data transmission, preferably electrically, to a control unit arranged/accommodated in the housing of the light unit. In this way, the position detection device is arranged close to the control unit so that the manufacturing expenditure of the surgical light is further reduced.

When, in turn, the control unit is coupled to the light sources to control the latter so that (in the operating condition) at least one light characteristic of the light unit, such as a size of light field generated, a light color or a number of the energized light sources, is adjusted/adjustable in response to a control instruction output by the control unit, the appropriate light characteristics of the light unit thus are controlled especially directly.

When the control unit is additionally programmed so that it adjusts the at least one light characteristic in response to the distance between the reference section and the ceiling determined by means of the position detection device in an operating condition of the surgical light, the control is further simplified.

Moreover, the control unit is advantageously connected to a reset device which during operation of the surgical light enables a target state of the surgical light to be defined by detecting an actual state of the distance relative to the ceiling and, at the same time, storing the at least one/plural adjusted light characteristic/s of the light unit. Further preferred, the reset device includes a reset button or a speech instruction input device such as a loudspeaker and, in turn, is connected electrically/for data transmission to the control unit. In this way, the control of the surgical light is further simplified.

In other words, during operation of a surgical light according to the invention, the light unit of the surgical light is initially adjusted optimally relative to an operating field and, for example, a reference point is set, i.e. a reference measurement to the ceiling is carried out. If the distance varies relative to the ceiling when the surgical light is reset, the lighting settings/light characteristics are appropriately tracked and adapted/optimized.

Hereinafter the invention shall be illustrated in detail by way of a FIGURE, and in this context also various example configurations will be described.

The single FIG. 1 illustrates a lateral view of a surgical light according to the invention in accordance with a preferred example configuration, wherein various possible positions of the position detection device are schematically represented at the retaining arm system as well as at a light unit of the surgical light. The FIGURE is merely schematic and serves exclusively for the comprehension of the invention.

In FIG. 1, a surgical light 1 as set forth in an example configuration according to the invention is illustrated. The surgical light 1 is prepared to be attached/fastened to a ceiling 5 of a room, for example an operating room, in a hospital. In FIG. 1, the surgical light 1 is already attached to the ceiling 5 of the room. Alternatively, in further configurations the surgical light 1 is also designed for fastening to a wall or a floor of the room, however.

The surgical light 1 according to FIG. 1 includes an anchoring element 4 which is fastened, in the operating state of the surgical light 1, directly to the ceiling 5. A retaining arm system 6 is connected to the anchoring element 4. The retaining arm system 6 is pivotably arranged/supported with a first end/end portion on the anchoring element 4. At a second end/end portion opposed to the first end a light unit 2 of the surgical light 1 is pivotably arranged/supported on the retaining arm system 6.

The light unit 2 forms a light/lighting device/lamp which in turn per se comprises plural individual light sources, viz. LED. In a light source one single LED, alternatively also plural LED, is/are provided and combined with a single (associated) optical lens system. In this way, each light source generates, in its energized state during operation of the surgical light 1, a bundled/parallel-directed light beam. The individual light sources are arranged/accommodated to be distributed in a housing 3 of the light unit 2. The light unit 2, which in turn is evident in FIG. 1, substantially is an umbrella-type light. Consequently, the housing 3 has a curved extension. The housing 3 in total extends along a ball segment.

The light sources are arranged in the housing 3 such that all of them are directed with their respective light outlet/their lens optics to a joint light emission side 9 of the housing 3. Said light emission side 9 of the housing 3 is the concave lower side 9 of the housing 3. Thus, during operation of the surgical light 1, the light sources in their activated state produce a light beam which is emitted toward the joint light emission side 9. The light sources of the light unit 2 thus produce light directed to a joint imaginary horizontal lighting plane (e.g. a surface of an operating table).

The side of the housing 3 facing away from the light emission side 9 is referred to as upper side 10. Said upper side 10 is a convex side of the housing 3 extending in umbrella shape.

For pivotably and movably bearing the light unit 2 on the anchoring element 4, the gimbal retaining arm system 6 is provided. The retaining arm system 6 includes a tubular base portion 16 which in turn is fastened tightly, viz. in a preferably rotationally and movably fixed manner, to the anchoring element 4. Alternatively, the base portion 16 may also be part of the anchoring element 4, wherein the base portion in such case is preferably formed integrally with the anchoring element 4.

At the base portion 16 plural supporting arm portions 14a to 14d are movably arranged relative to the base portion 16 as well as relative to each other. A first supporting arm portion 14a is configured at the second end of the retaining arm system 6 and is attached to the light unit 2. The light unit 2 to this end has a bearing point 12 which forms a pivot axis extending into the plane of projection in FIG. 1. The bearing point 12 is configured by a pin-shaped projection which is tightly attached to the housing 3. The bearing point 12 thus forms a first (single-axis) swivel joint 17.

A second supporting arm portion 14b of the retaining arm system 6 in turn is pivotally/rotatably coupled to the first supporting arm portion 14a. A second swivel joint 18 which may also be a universal joint serves for this purpose. The second supporting arm portion 14b is substantially bent in L shape. The second supporting arm portion 14b in turn is connected to a third supporting arm portion 14 via a third swivel joint 19. The third swivel joint 19 is configured as a (first) universal joint 15a. The third supporting arm portion 14c in turn is articulated to a fourth supporting arm portion 14d via a fourth swivel joint 20. The fourth swivel joint 20, too, is configured as a (second) universal joint 15b. The fourth supporting arm portion is pivoted about an axis of rotation (single-axis) relative to the base portion 16 by means of a fifth swivel joint 21. The interaction of the supporting arm portions 14a to 14d as well as of the swivel joints 17 to 21 results in the gimbal retaining arm system 6 which permits versatile positioning of the light unit 2 in space.

According to the invention, as indicated in FIG. 1 by the three reference sections 8; 8a, 8b, 8c, in addition at least one position detection device 7/position determination device is provided at the surgical light 1. The position detection device 7 is designed and arranged such that in the operating state it detects a value for determining a distance between a reference section 8; 8a, 8b, 8c at the light unit 2 or at the retaining arm system 6 and the ceiling 5. As indicated in FIG. 1, the position detection device 7 may comprise plural, viz. three, sensors 11, 13 or 22 detailed hereinafter at the reference sections 8a, 8b and 8c, or alternatively may comprise only some/individual sensors 11, 13 and/or 22. The respective sensor 11, 13 or 22 always serves for detecting a value which in turn is used to determine/refer to the position/height of the light unit 2.

At a first reference portion 8a of the surgical light 1, a (first) distance detection sensor 11 of the position detection device 7 is provided which is capable of directly detecting a distance from an object. The first distance detection sensor 11 is shown merely by means of a reference arrow for the sake of clarity. Especially, the first distance detection sensor 11 is arranged in the housing 3. The first distance detection sensor 11 is designed as an infrared sensor. The first distance detection sensor 11 has a measuring range (length/extension of the measuring field detection area) of at least 1.50 m, preferably of at least 2 m. The first distance detection sensor 11 is arranged toward the upper side 10 of the housing 3. The first distance detection sensor 11 includes a measuring field detection area which is always oriented with at least a particular proportion opposite to the acting gravitation, i.e. spatially upwards in the intended mounting position. The first distance detection sensor 11 therefore directly detects a height adjustment of the light unit 2 by measuring the relative distance between the first reference section 8a/the housing 3 and the ceiling 5.

In this example configuration, the light unit 2 cannot be fully pivoted about 360° but only in such range, e.g. anti-clockwise as well as clockwise about 165° in the plane according to FIG. 1, that in each pivoting position of the light unit 2 a directional component of the measuring field detection area of the first distance detection sensor 11 is directed toward the ceiling 5. The first distance detection sensor 11 is arranged on the housing 3 along the imaginary pivot axis.

The first distance detection sensor 11 thus continuously determines, when the surgical light 1 is activated, a distance of the first reference section 8a/of the housing 3 (in the area of the pivot axis) relative to the ceiling 5.

At a second reference section 8b which is provided adjacent to the second swivel joint 18, i.e. at the second supporting arm portion 14b, another (second) distance detection sensor 13 of the position detection device 7 is arranged. The second distance detection sensor 13 is structured and functions just as the first distance detection sensor 11. The second distance detection sensor 13 is arranged on an upper side of the second supporting arm portion 14b, i.e. a side of the second supporting arm portion 14b facing a ceiling 5 in the operating state. The second supporting arm portion 14b is appropriately displaced, when the light unit 2 is lowered or raised, equally in height (in space)/in its distance relative to the ceiling 5. The second distance detection sensor 13 in turn serves for directly detecting the distance between the second reference section 8b (at the second supporting arm portion 14b) and the ceiling 5. Said second distance detection sensor 13 of the position detection device 7 basically may also be arranged at any number of further positions of the second supporting arm portion 14b and, resp., of the other supporting arm portions 14a to 14d, however.

The position detection device 7 thus includes, when using the respective distance detection sensor 11 and, resp., 13, a sensor 11, 13 arranged toward an upper side, i.e. to an upwardly projected side of the surgical light 1. By the direction "upwardly" especially a direction opposite to the acting gravitation/gravitational force and, resp., a vertical direction in a spatial coordinate system is meant.

At the third reference section 8c which is provided in the area of the third swivel joint 19 and, resp., is integrated in the third swivel joint 19, the position detection device 7 includes an angle detection sensor 22 as an alternative or in addition to the respective distance detection sensor 11, 13. The third reference section 8c in this configuration is a swivel joint of the retaining arm system 6. The angle detection sensor 22 serves for indirectly determining the distance between the first swivel joint 19/the third reference section 8c and the ceiling 5. The angle detection sensor 22 detects a (relative) angular position/an angle between a longitudinal axis of the linearly extending third supporting arm portion 14c and a reference line (e.g. an imaginary straight line defined by the anchoring element 4 or a longitudinal axis of the base portion 16) so that the current position/location/height of the light unit 2 can be indirectly concluded. The further reference calculation of the actual distance between the ceiling 5 and the third reference section 8c by way of the angular position measured then is preferably carried out by the position detection device 7 or alternatively in a control unit connected thereto and detailed hereinafter.

The angle detection sensor 22 may be basically provided in addition or as an alternative to the first and/or second distance detection sensor 11, 13 in the surgical light 1/position detection device 7.

As an alternative to the third swivel joint 19 forming the first universal joint 15a, it is also possible to provide the angle detection sensor 22 in a different portion of the retaining arm system 6, such as in/at the fourth swivel joint 20.

The position detection device 7 is typically further connected for data transmission, viz. electrically, to a control unit not shown here in detail for the sake of clarity. The control unit is arranged in the housing 3 of the light unit 2. The control unit in this way interacts with the light sources to control the same so that the control unit acts to adjust plural light settings/characteristics/lighting settings of the light unit 2 in the operating state (in response to the height of the light unit 2 relative to the ceiling 5 detected/determined by the position detection device 7). The light characteristics adjustable by the control unit in this example configuration are at least a size of light field generated (of the light field generated by the energized light sources), a light color (of a generated light field) as well as a number of the energized light sources. The control unit is programmed so that it adjusts the respective light characteristic in response to the distance between the reference section 8; 8a, 8b, 8c and the ceiling 5 determined by means of the position detection device 7 in the operating state of the surgical light 1.

Moreover, the control unit is advantageously connected to a reset device which, when the surgical light 1 is activated, enables a target state of the surgical light 1 to be defined by detecting an actual state of the distance relative to the ceiling 5 and, at the same time, storing the currently adjusted light characteristics of the light unit 2 together with the distance value (and, resp., a height value). The reset device includes a reset button and/or a speech instruction input device such as a loudspeaker and, in turn, is connected electrically/for data transmission to the control unit.

In other words, in a surgical light 1 according to the invention a sensor 11, 13 is thus arranged for measuring the distance of the light unit 2 relative to the ceiling 5. Said sensor 11, 13 for distance measurement is located e.g. on the rear side/upper side 10 of the surgical light 1 or at either of the universal joints 15a, 15b of the surgical light 1. Equally, also the angle of the height-adjustable spring arm in the form of the third supporting arm portion 14c could be detected (by a sensor 22) so as to determine the height of the surgical light 1 (by means of the control unit).

LIST OF REFERENCE NUMERALS 1 surgical light
2 light unit
3 housing
4 anchoring element
5 ceiling
6 retaining arm system
7 position detection device
8 reference section
8a first reference section
8b second reference section
8c third reference section
9 light emission side/lower side
10 upper side
11 first distance detection sensor
12 bearing point
13 second distance detection sensor
14a first supporting arm portion
14b second supporting arm portion
14c third supporting arm portion
14d fourth supporting arm portion
15a first universal joint
15b second universal joint
16 base portion
17 first swivel joint
18 second swivel joint
19 third swivel joint
20 fourth swivel joint
21 fifth swivel joint
22 angle detection sensor

The invention claimed is:

1. A surgical light comprising a light unit which has a plurality of light sources individually accommodated in a housing, wherein each light source is arranged and oriented in such way that the light source produces a light beam in an energized state, an anchoring element which is prepared for fastening to a ceiling, a wall or a floor of a room, a retaining arm system which connects the light unit slidably and/or pivotably to the anchoring element, and a position detection device that has a distance detection sensor is arranged and designed in such way that, in the operating state, the distance detection sensor determines a distance of a reference section of the light unit from the ceiling, wherein the housing has a curved extension, with the light sources producing light beams which are emitted toward a joint light emission side of the housing, and the distance detection sensor which is arranged on an upper side of the housing faces away from the light emission side.

2. The surgical light according to claim 1, wherein the first distance detection sensor is arranged in the area of a pivot axis about which the light unit is pivoted relative to the retaining arm system.

3. The surgical light according to claim 2, wherein the position detection device includes a second distance detection sensor provided on the retaining arm system.

4. The surgical light according to claim 1, wherein the position detection device includes a second distance detection sensor provided on the retaining arm system.

5. The surgical light according to claim 4, wherein the second distance detection sensor is arranged on a universal joint of the retaining arm system.

6. The surgical light according to claim 1, wherein the position detection device includes an angle detection sensor which is designed and arranged such that it detects an angle of a supporting arm portion of the retaining arm system arranged pivotably relative to the anchoring element.

7. The surgical light according to claim 1, wherein the position detection device is connected for data transmission to a control unit arranged in the housing of the light unit.

8. The surgical light according to claim 7, wherein the control unit is coupled to the light sources to control the light sources such that at least one light characteristic of the light unit can be adjusted in response to a control instruction output by the control unit.

9. The surgical light according to claim 8, wherein the control unit is programmed so that it adjusts the at least one light characteristic in response to the distance between the reference section and the ceiling determined by means of the position detection device in an operating state of the surgical light.

10. The surgical light according to claim 7, wherein the control unit is programmed so that it adjusts the at least one light characteristic in response to the distance between the reference section and the ceiling determined by means of the position detection device in an operating state of the surgical light.

11. The surgical light according to claim 1, wherein the position detection device includes an angle detection sensor which is designed and arranged such that it detects an angle of a supporting arm portion of the retaining arm system arranged pivotably relative to the anchoring element.

12. An apparatus comprising:
a light unit comprising a plurality of light sources individually accommodated in a housing, wherein each light source is arranged and oriented to produce a light beam in an energized state;
an anchoring element configured to be fastened to a surface;
a retaining arm system configured to connect the light unit slidably and/or pivotably to the anchoring element; and
a position detection device configured to determine a distance of a reference section of the light unit or of the retaining arm system from the surface,
wherein the housing has a curved extension, with the light sources producing light beams which are emitted toward a joint light emission side of the housing, and a distance detection sensor which determines a distance of a reference section of the light unit from the ceiling and is arranged on an upper side of the housing faces away from the light emission side.

13. The apparatus of claim 12, wherein the position detection device comprises a second distance detection sensor provided on the retaining arm system, wherein the second distance detection sensor is configured to detect a second height adjustment of the light unit.

14. The apparatus of claim 13, wherein the position detection device comprises an angle detection sensor configured to detect an angle of a supporting arm portion of the retaining arm system arranged pivotably relative to the anchoring element.

15. An apparatus comprising:
a light unit comprising a plurality of light sources individually accommodated in a housing;
an anchoring element configured to be fastened to a surface;
a retaining arm system configured to connect the light unit slidably and/or pivotably to the anchoring element; and
a position detection device configured to determine a distance of a reference section of the light unit from the surface, wherein the housing has a curved extension, with the light sources producing light beams which are emitted toward a joint light emission side of the housing, and a distance detection sensor which determines a distance of a reference section of the light unit from the ceiling and is arranged on an upper side of the housing faces away from the light emission side.

* * * * *